(12) United States Patent
Chan et al.

(10) Patent No.: US 6,589,729 B2
(45) Date of Patent: Jul. 8, 2003

(54) METHODS, DEVICES, AND SYSTEMS FOR MONITORING TIME DEPENDENT REACTIONS

(75) Inventors: Samuel D. H. Chan, Daly City, CA (US); Ring-Ling Chien, San Jose, CA (US); Andrea W. Chow, Los Altos, CA (US); Benjamin N. Wang, Palo Alto, CA (US)

(73) Assignee: Caliper Technologies Corp., Mountain View, CA (US)

( * ) Notice: Subject to any disclaimer, the term of this patent is extended or adjusted under 35 U.S.C. 154(b) by 162 days.

(21) Appl. No.: 09/774,531

(22) Filed: Jan. 31, 2001

(65) Prior Publication Data

US 2001/0051338 A1 Dec. 13, 2001

Related U.S. Application Data

(60) Provisional application No. 60/180,235, filed on Feb. 4, 2000, provisional application No. 60/182,086, filed on Feb. 11, 2000, and provisional application No. 60/211,827, filed on Jun. 15, 2000.

(51) Int. Cl.$^7$ ................................................ C12Q 1/00
(52) U.S. Cl. ........................................ 435/4; 435/288.5
(58) Field of Search ............................ 435/7.2, 287.3, 435/4, 288.2, 288.5, 286.1

(56) References Cited

U.S. PATENT DOCUMENTS

| 4,906,344 A | 3/1990 | Hjerten |
| 5,304,487 A | 4/1994 | Wilding et al. |
| 5,498,392 A | 3/1996 | Wilding et al. |
| 5,635,358 A | 6/1997 | Wilding et al. |
| 5,637,469 A | 6/1997 | Wilding et al. |
| 5,726,026 A | 3/1998 | Wilding et al. |
| 5,779,868 A | 7/1998 | Parce et al. |
| 5,804,436 A | 9/1998 | Okun et al. |
| 5,919,646 A | 7/1999 | Okun et al. |
| 5,921,678 A | 7/1999 | Desai et al. |
| 5,928,880 A | 7/1999 | Wilding et al. |
| 5,942,443 A | 8/1999 | Parce et al. |
| 6,096,509 A | 8/2000 | Okun et al. |
| 6,242,209 B1 | 6/2001 | Ransom et al. |
| 6,280,967 B1 | 8/2001 | Ransom et al. |

FOREIGN PATENT DOCUMENTS

| WO | WO 9604547 | 2/1996 | |
| WO | WO 9800231 | 1/1998 | |
| WO | WO 98/52691 | * 11/1998 | ............. B01L/3/00 |
| WO | WO 99/61888 | * 12/1999 | .......... G01N/15/14 |
| WO | WO 9967639 | 12/1999 | |
| WO | WO 0058719 | 10/2000 | |

OTHER PUBLICATIONS

Segel, *Biochemical Calculations* 2$^{nd}$ Edition, (1976) John Wiley and Sons.

* cited by examiner

*Primary Examiner*—Ralph Gitomer
(74) *Attorney, Agent, or Firm*—Matthew B. Murphy; Andrew L. Filler

(57) ABSTRACT

Methods for monitoring time dependent reactions that comprise providing a flow channel, typically microscale in dimension, flowing at least two reagents into the flow channel and varying the flow rate of the mixture through the flow channel. By increasing and/or decreasing the flow rate of the reagent mixture from the point of mixing to the point of detection, one alters the amount of reaction time, allowing monitoring reaction kinetics over time.

23 Claims, 9 Drawing Sheets

METHODS, DEVICES, AND SYSTEMS FOR MONITORING TIME DEPENDENT REACTIONS

CROSS-REFERENCE TO RELATED APPLICATIONS

This application claims priority to Provisional U.S. Patent Application No. 60/180,235, filed Feb. 4, 2000; No. 60/182,086, filed Feb. 11, 2000; and No. 60/211,827, filed Jun. 15, 2000, each of which is hereby incorporated herein by reference in its entirety for all purposes.

BACKGROUND OF THE INVENTION

The biological and chemical sciences, much like the electronics industry, have sought to gain advantages of cost, speed and convenience through miniaturization. The field of microfluidics has gained substantial attention as a potential solution to the problems of miniaturization in these areas, where fluid handling capabilities are often the main barrier to substantial miniaturization.

For example, U.S. Pat. Nos. 5,304,487, 5,498,392, 5,635,358, 5,637,469 and 5,726,026, all describe devices that include mesoscale flow systems for carrying out a large number of different types of chemical, and biochemical reactions and analyses.

Published international patent application No. WO 96/04547 to Ramsey describes microfluidic devices that incorporate electrokinetic means for moving fluids or other materials through interconnected microscale channel networks. Such systems utilize electric fields applied along the length of the various channels, typically via electrodes placed at the termini of the channels, to controllably move materials through the channels by one or both of electroosmosis and electrophoresis. By modulating the electric fields in intersecting channels, one can effectively control the flow of material at intersections. This creates a combination pumping/valving system that requires no moving parts to function. The solid state nature of this material transport system allows for simplicity of fabricating microfluidic devices, as well as simplified and more accurate control of fluid flow.

Published international patent application No. WO 98/00231 describes the use of microfluidic systems in performing high throughput screening of large libraries of test compounds, e.g., pharmaceutical candidates, diagnostic samples, and the like. By performing these analyses microfluidically, one gains substantial advantages of throughput, reagent consumption, and automatability.

Despite the above-described advances in the field of microfluidics, there still exist a number of areas where this technology could be improved. For example, while electrokinetic material transport systems provide myriad benefits in the microscale movement, mixing and aliquoting of fluids, the application of electric fields can have detrimental effects in some instances. For example, in the case of charged reagents, electric fields can cause electrophoretic biasing of material volumes, e.g., highly charged materials moving at the front or back of a fluid volume. Solutions to these problems have been previously described, see, e.g., U.S. Pat. No. 5,779,868. Alternatively, where one is desirous of transporting cellular material, elevated electric fields can, in some cases, result in a perforation or electroporation, of the cells, which may affect their ultimate use in the system.

In addition to these difficulties of electrokinetic systems, microfluidic systems, as a whole, have largely been developed as relatively complex systems, requiring either complex electrical control systems or complex pump and valve systems, for accurately directing material into desired locations. Accordingly, it would be generally desirable to provide microfluidic systems that utilize simplified transport systems, but that are also useful for carrying out important chemical and/or biochemical reactions and other analyses. The present invention meets these and a variety of other needs.

SUMMARY OF THE INVENTION

In a first aspect, the present invention provides for a method of monitoring a time-dependent reaction. The method comprises introducing first and second reagents into a first flow channel wherein the reaction is initiated with respect to at least a first reagent, to form a first reaction mixture. The first mixture is transported along the flow channel, past a detection zone which detects an extent of the reaction. The flow rate of the first mixture is varied along the flow channel to vary an amount of time between mixing of the first and second components and detection of the extent of the reaction at the detection zone. The result of an interaction is then monitored between the first and second reagents.

Another aspect of the present invention is a system for monitoring a time dependent reaction. The system comprises a body containing at least a first flow channel. The first flow channel is fluidly connected to a source of a first reagent and a source of a second reagent. A flow controller is operably coupled to the flow channel, which contains programming to provide a varying flow rate of a fluid into and through the flow channel.

BRIEF DESCRIPTION OF THE FIGURES

FIG. 1A shows two reagents being brought together in a flow channel, e.g., from two flow channels connected to a main flow channel; FIG. 1B illustrates a situation where the flow rate is increased through the main flow channel of FIG. 1A; FIG. 1C illustrates the situation where the flow rate is decreased through the main flow channel of FIG. 1A.

DETAILED DESCRIPTION OF THE INVENTION

I. General Description

The present invention generally provides methods for monitoring time dependent reactions. Monitoring of time-dependent reactions is particularly useful in the analysis of reaction kinetics in chemical, biochemical and biological interactions, in order to ascertain the mechanics of those reactions and further elucidate affectors of those reactions.

Generally, the methods of the present invention typically comprise flow through assay methods where the reactants, e.g., first and second reagents, are flowed concurrently into and through a flow channel, whereupon the reagents mix in a reaction mixture. The reagents interact and react to produce products of the particular reaction. The amount of product produced in a given reaction is a measure of the extent of the reaction that is being analyzed. The reaction mixture is flowed past a detection zone at which the accumulated products (or depleted reactants) of the reaction are detected. The reaction time is the length of time between the initiation of the reaction of interest, e.g., the mixing of reactive reagents, and the detection time.

Although generally described herein as a reaction between two reagents, it will be appreciated that the methods described herein are equally applicable to reactions carried out on a single reagent, e.g., reactions that are initiated by means other than combination with another reagent. Such method of initiating reactions include, e.g., photoactivated reactions, where a particular reagent is rendered more reactive by virtue of exposure to light, as well as thermally activated reactions that are activated by heat. Similarly, the response of the reagent(s) to external stimuli such as light and/or heat can be measured as the reaction of interest, e.g., photo or thermal degradation of reagents, etc.

Figure 1A:
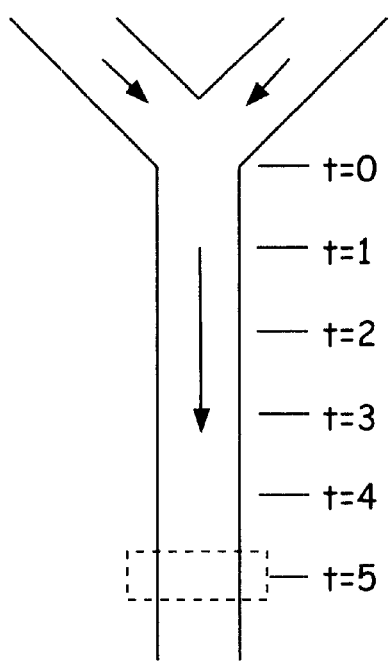
FIGS. 1A–1C schematically illustrate the principles of flow rate variation as it relates to reaction parameters, in accordance with the present invention.
Figure 1B:
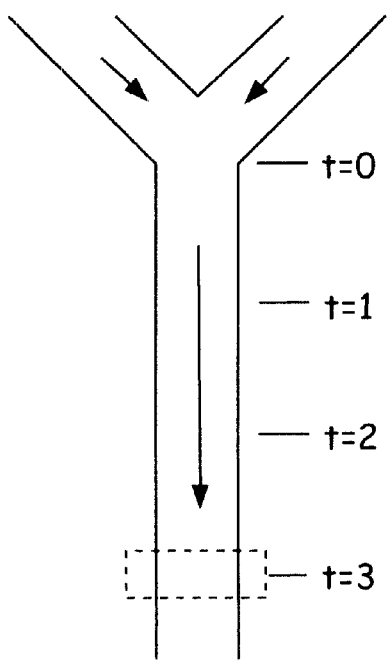
Figure 1C:
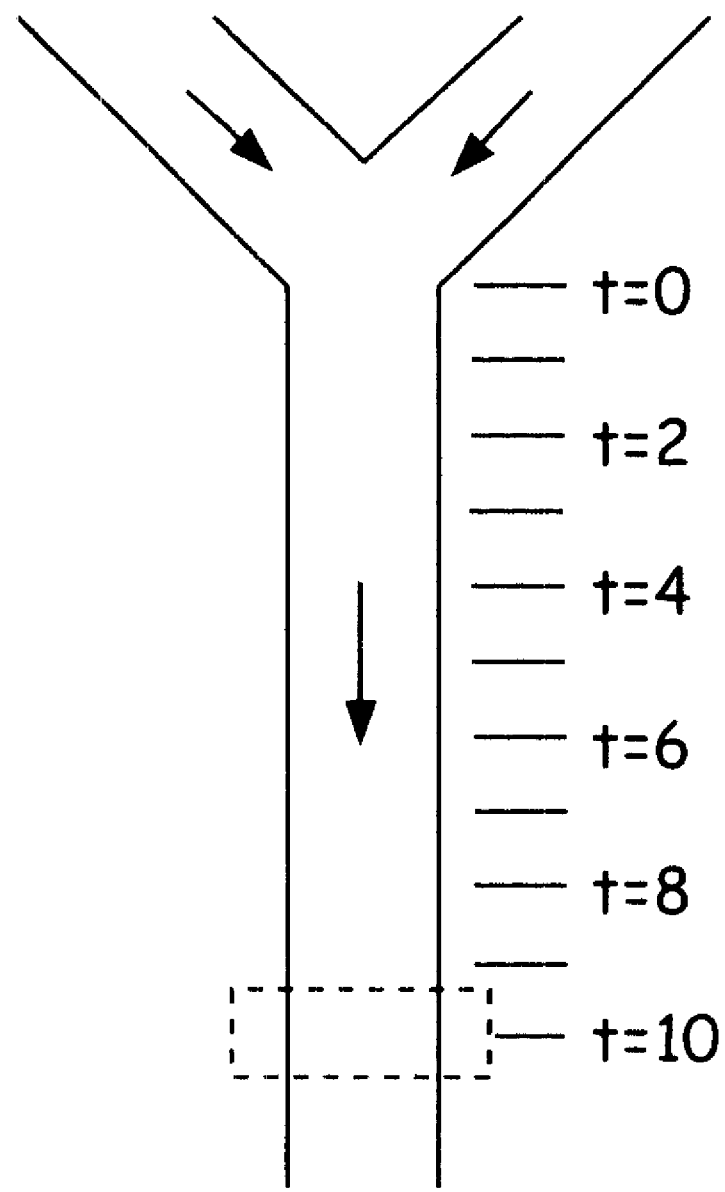

When the flow rate of the flowing mixture through the flow channel is maintained constant, the extent of the reaction detected at the detection zone will remain constant, barring any other intervention in the reaction. In accordance with the present invention, however, a time course for the reaction is obtained by varying the flow rate of the reaction mixture through the flow channel and past the detection point, e.g., either slowing it down or speeding it up, thus giving the reaction mixture a longer or shorter time frame in which to react. FIGS. 1A, 1B and 1C schematically illustrate the effect of flow rate variations (indicated by arrows of differing length within the main channel) on the extent of a reaction that is detected in the systems described herein. For example, in FIG. 1A, two reagents are shown being brought together in the flow channel, e.g., from two flow channels connected to a main flow channel. At a given flow rate, the amount of time "t", e.g., in seconds or minutes, that the reagents are allowed to react at particular positions of the channel is shown to the right of the main channel. A detection window or zone is shown as a dashed box. FIG. 1B illustrates a situation where the flow rate is increased, e.g., to 1.67 times the original flow rate. In doing so, the reagents are allowed to react for a shorter amount of time before they move past the detection zone, because they are moving faster. Conversely, FIG. 1C illustrates a situation where the reagents are moving more slowly, thus allowing them more time to react within the channel prior to moving through the detection zone.

In accordance with the present invention, flow rate of the reaction mixture is typically varied in order to monitor the extent of a given reaction at different reaction times. In particularly preferred aspects, this variation of flow rate is done in real time, or "on-the-fly," meaning that the operation of the system is not stopped during the flow rate variation. Also, although the flow rate may be varied in steps, e.g., sharp increases or decreases in flow rate, in preferred aspects, the present invention is directed to a more gradual ramping up or down of the flow rate. In similarly preferred aspects, the flow rates are varied in accordance with pre-designated or programmed instructions so as to produce a desired flow-rate profile of reaction mixture through the main flow channel.

In an alternate aspect, different time points of a given reaction are monitored by monitoring different positions within the flow channel. This may be accomplished using multiple detectors to detection reaction results, or by using a single detector that is movable among the different points along the channel.

II. Systems

As noted above, the present invention typically utilizes a flow channel to contain the reaction mixtures of interest. The various reagents that make up the reaction mixture are introduced into the main reaction channel via one or more connecting channels. In a simple embodiment, the flow channel comprises a single flow conduit, i.e., a tube, capillary or other flow channel that is separately connected to the reagent sources so as to allow concurrent introduction of the various reagents into the main flow channel such that the reagents mix within or just prior to their introduction into the main flow channel.

In particularly preferred aspects, the flow channels and connecting channels are incorporated into an integrated microfluidic device. As used herein, the term "microfluidic" typically refers to a fluid passageway or conduit that has at least one microscale cross-sectional dimension, e.g., from about 0.1 to about 500 $\mu$m. Integrated microfluidic devices typically comprise a network of microscale fluidic elements, e.g., conduits, chambers or the like, that are fluidly coupled to one another. While such systems may be embodied in an aggregation of separate elements, e.g., capillaries, chambers, etc., in preferred aspects, they are integrated into a single planar body structure. Typically, these planar body structures are fabricated from an aggregation of substrate layers having features fabricated on their surfaces such that the fluidic elements are defined at the interfaces of the substrate layers. In particular, a planar surface of one or more of the substrate layers is fabricated to define a series of grooves and or depressions therein. A planar surface of a second substrate layer is then overlaid and bonded to the surface of the first to seal the grooves or depressions to form the sealed channels or chambers of the device.

Figure 2:
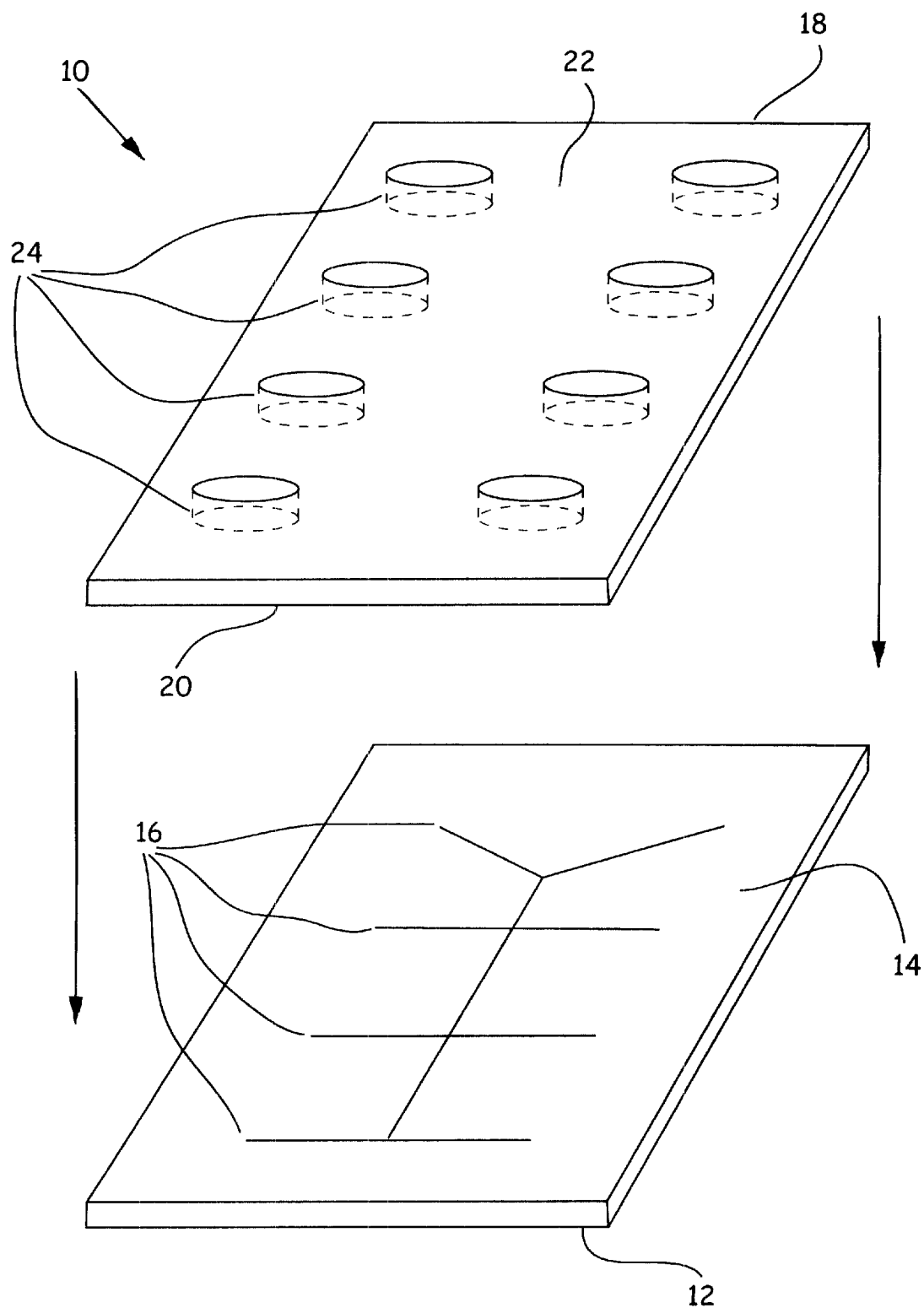
FIG. 2 schematically illustrates the layered construction of a simple microfluidic device.

FIG. 2 schematically illustrates a device incorporating this layered structure. As shown, the device 10 includes a first planar substrate 12 having an upper surface 14. A plurality of grooves and/or depressions 16 are defined in the upper surface 14 of the first substrate 12. A second substrate 18 having a lower planar surface 20 and an upper planar surface 22 is then placed upon the upper surface 14 on the lower substrate 12 and the substrates are bonded together to seal the grooves/depressions to define channels/chambers within an interior portion of the overall body structure. The upper surface 22 of the second substrate 18 may include one or more wells or reservoirs 24 which are configured to be in fluid communication with the channel network defined by channels 16 in the lower substrate 12. Although described in terms of grooves or depressions fabricated into the surface of one of the substrate layers, it will be appreciated that grooves may be provided in either or both of the opposing surfaces of the two substrates so as to define more complex channel networks. Also, although illustrated as a single interconnected channel network, it will be appreciated that a single integrated device may include several discrete, e.g., completely separate, channel networks or individual channels.

Figure 3:
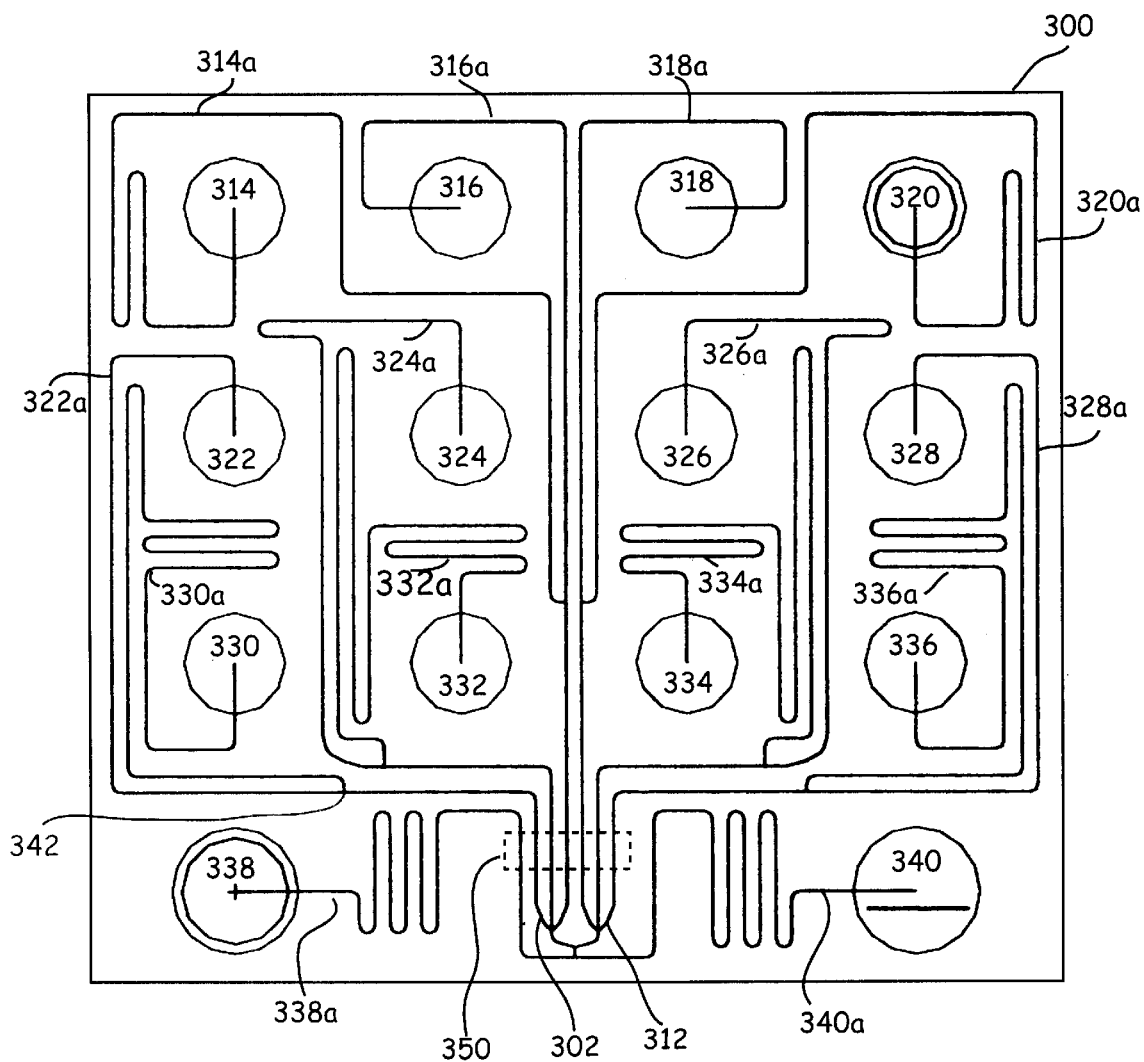
FIG. 3 schematically illustrates the channel layout for a microfluidic device that is particularly useful in practicing the methods of the present invention.

FIG. 3 is a schematic illustration of a microfluidic device channel network that is particularly suited for the methods of the present invention. As shown, the device 300 includes a plurality of different reservoirs 314–340, disposed in the body of the device 300. As shown, the reagent reservoirs 314–336 are grouped in pairs, e.g., reservoirs 314:316, 318:320, 322:330, etc.

Each of the reservoir pairs, e.g., pair 314:316, is fluidly connected via associated channels, e.g., channels 314a and 316a, respectively, to one of a plurality of analysis channels, e.g., channels 302–312. Each of the plurality of analysis channels is then coupled to one or more waste reservoirs, e.g., reservoirs 338 and 340, via one or more waste channels, e.g., channels 338a and 340a. A detection window or region 350 also exists over each of the analysis channels 302–312, in order to observe the signals emanating from those channels, e.g., fluorescent signals. Operation of the device shown in FIG. 3 in accordance with the present invention is described in greater detail, below.

In carrying out the methods described herein, it is generally useful to couple a fluid transport system to the flow channels described above. Typically, these flow systems are capable of directing the reaction mixtures through the main channel portions at varying flow rates. As noted above, in preferred aspects, the flow systems are capable of being adjusted on-the-fly, either manually or in accordance with preprogrammed flow profiles that are input by a user. Typically, the flow systems comprise a flow controller that is operably coupled to at least the main flow channel in which the reaction monitoring is being carried out. By "operably coupled" is meant that the flow controller is coupled to the channel in a way that permits the application of a flow driving force to the contents of the flow channel so as to cause material movement through that channel.

As noted above, the controller instrument may include one or more of a variety of different flow system types. For example, in certain preferred aspects, the flow controller includes a vacuum or pressure source that is operably coupled to one or more channels of the microfluidic device during operation to push or draw fluid through the channels of the device. In alternative preferred aspects, the controller comprises a source of electrical power that is operably coupled to the channels of the device, e.g., via electrodes inserted into reservoirs at the termini of channels, to move fluid or other materials through the channels of the device via electrokinetic forces, i.e., electrophoresis and/or electroosmosis.

In the case of a vacuum or pressure source, this typically comprises vacuum or pressure pump integrated into the instrument. Typically, commonly used pumps, such as syringe pumps, peristaltic pumps or the like are preferred for use in these applications. In accordance with the present invention, these pumps also are capable of varying the amount of pressure or vacuum supplied to the channels of the device, and thereby vary the flow rate of material through those channels, e.g., an increase in the pressure differential increases the flow rate, while a decrease in the pressure differential results in a decreased flow rate. The variation of the flow rate is generally carried out in accordance with a user input flow profile that is programmed either into the controller unit or into a computer that is operably coupled to the controller. By "user input" is meant that a flow profile instruction is provided to the controller instrument trough a programming step, e.g., as firmware or software that is input by the end-user or during the manufacturing process for the controller instrument or its associated computer.

The pressure or vacuum sources are typically provided operably coupled to one or more of the channels of the microfluidic device to control flow therethrough. For example, with respect to the microfluidic device illustrated in FIG. 3, one or more pressure sources may be provided coupled to ports 314–340 in order to provide a pressure differential through the channels connected to those ports. Appropriate control of the pressures applied at the ends of the various channels permits control of the relative flow of material through those channels.

In particularly preferred aspects, flow rate within interconnected channels is controlled at a single port to the channels, e.g., a common waste port. Specifically, again with reference to FIG. 3, a negative pressure or vacuum is applied at a terminal or waste reservoir or port, e.g., reservoir 338 and/or 340. This vacuum draws fluid through the various channels of the device, e.g., channels 302–312 toward the waste reservoirs. The various channels are configured such that fluid flows through the channels at a predetermined rate relative to other channels under the applied vacuum. Typically, the configuration of these channels involves providing the channels with a selected length or cross-section so as to dictate the relative flow rate through the channel.

Such channel configuration is described in detail in, e.g., U.S. patent application Ser. No. 09/238,467, filed Jan. 28, 1999, which is incorporated herein by reference in its entirety for all purposes.

In the case of electrically controlled flow systems, varying flow rates within the channels of the device is typically accomplished by varying the electrokinetic force applied to the material in the channel. This is typically accomplished by increasing or decreasing the voltage drop across the length of a particular channel through which material is being moved. Variation of applied voltages or current flow through a channel is also typically accomplished in accordance with a user input flow profile. Connection of the channels to electrical power sources is typically accomplished by providing electrodes that are connected to the power supply in direct contact with fluid within the reservoirs of the device, e.g., reservoirs 314–340 of FIG. 3.

The flow channel in which the particular reaction is being monitored includes a detection zone at which the results of the operation are detected. The detection zone is marked by the presence of a detection system that is positioned so as to be in sensory communication with the contents of the flow channel at the detection zone. As used herein, the phrase "within sensory communication" refers to a detection system that is positioned so as to monitor a particular detectable event within the detection zone. These detectable events may be optical (e.g., fluorescent signals, absorbance characteristics, colored signals, light scattering signals, or other changes in optical characteristics, e.g., refractive index, etc.), thermal, electrochemical (conductivity), chemical (chemical constituents, e.g., oxygen, etc.) or physical (viscosity, etc.) in nature.

In the case of optical signals, a detection system that is in sensory communication with a particular material is positioned so as to receive a sufficient quantity of the optical signal so as to detect its presence. Typically, this is carried out by positioning an optical detection system adjacent to a transparent or translucent portion of the flow channel, e.g., the detection zone. An optical signal is then transmitted through the transparent or translucent portion of the flow channel and collected and detected by the detection system. In the case of electrochemical or chemical detection, such systems often require the presence of specific sensors in direct physical contact with the contents of the flow channel, e.g., as monitoring electrodes, or the like, in order to be in sensory communication with the contents of the flow channel. Optical signals and detection systems are most preferred in the present invention for their ease of use, and physical (although not sensory) isolation from the contents of the flow channel. Although not required, in preferred aspects, the detection system is integrated with the flow controller system into a single instrument.

Detection may be carried out at a single point along the flow channel, e.g., using a point detector such as a laser based fluorescence detector. Such detection is useful where a single data point is required for determining analysis results. Alternatively, a wider area of the flow channel may be monitored for detecting the signal, e.g., using a scanning system that scans a larger portion of a channel, an imaging system such as a CCD or a linear laser based detector, where analysis of results requires observation of the signal within a given channel for a longer time period. In cases where multiple channels are being observed, either for multiple time points of a single reaction (as described with reference to FIG. 8) or among multiple different channels in which different reactions are being monitored, e.g., as shown in FIG. 3. A variety of linear laser detectors are known in the art, including, e.g., galvo-scanners, cylindrical lens detectors in combination with imaging systems, i.e., that focus excitation light in a linear pattern. In particularly preferred aspects, the controller/detector function is provided by a platform instrument available from, e.g., Agilent Technologies, Inc. and/or Caliper Technologies Corp. Specifically, for integrated microfluidic devices having sample sources incorporated therein, the device can be placed into a 2100 Bioanalyzer available from Agilent Technologies, Inc., optionally outfitted with a vacuum port for pressure/vacuum control of at least one port of the device. Alternatively, an HTS system available from Caliper Technologies Corp., under their Technology Access Program, permits the accession of libraries of sample materials contained in standard storage systems, e.g., multiwell plates (see www.calipertech.com).

Figure 8:
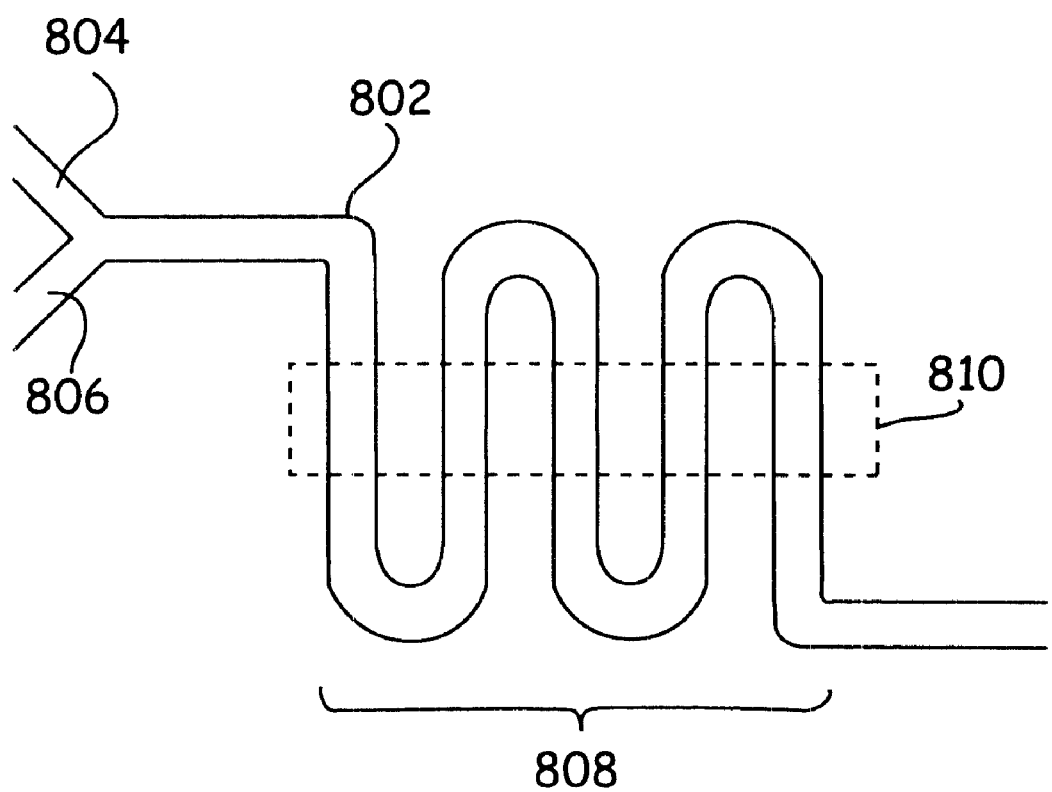
FIG. 8 illustrates an alternative system for monitoring time dependent reactions.

In addition, as noted above, another method of measuring different time points of a reaction involves moving the detector to different points along the flow channel while otherwise maintaining flow through the channel at a constant level. In particularly preferred aspects, the flow channel is arranged in a serpentine or reciprocating pattern at the detection zone, such that ensuing portions of the flow channel turn back and run parallel to the preceding portions of the channel. A detector is provided that can simply scan or step from one portion of the channel to another portion, etc., to detect the reaction results at that point. An example of a channel geometry for accomplishing this is shown in FIG. 8. Briefly, the flow channel 802 is connected to one or more reagent sources, e.g., via channels 804 and 806, and includes a serpentine detection region 808. The detection window 810 spans the various segments of the channel in the serpentine region 808. The geometry of the serpentine region and/or the flow rate through the flow channel can be varied to alter the time intervals between the detection points. A variety of scanning detection systems can be employed as the detection aspect of the system, including track mounted detectors, pivoting detectors and galvoscanner detectors.

III. Flow Rate Variation

As noted above, the present invention involves varying the rate of flow of reactants along a flow channel in order to monitor time dependent reactions involving those reactants (e.g., between two reactants, or involving only a single reactant). Specifically, at least a first reagent or reactant is flowed into the flow channel and a reaction is initiated at a first point in the flow channel. In typical cases, this involves the combination of the first reactant with at least a second reactant at a first point in a flow channel. Once the reaction is initiated, a "reaction mixture" is formed which includes the reagents and/or any products that result from the reaction. The reaction mixture is then continuously flowed along the channel past a detection zone. As noted herein, initiation of the reaction optionally involves combination of the first reagent with one or more additional reagents, but can also involve exposure of the first reagent to some external stimuli, e.g., light or heat energy. In continuous flow assays, the initiation of the reaction, whether based upon addition of reagents or otherwise takes place at a first point in the flow channel and is carried out continuously on the flowing stream of reagents. The detection of the results of the reaction is then carried out at a second point in the flow channel. By varying the flow rate of the reactants between the first and second points, one can vary the reaction time before detection. Similarly, by varying the location of the second point relative to the first point, one can detect reactions that have varying incubation/reaction times. Relatedly, one can simultaneously detect at multiple different points along the flow channel that differ in their locations relative to the first point, in order to simultaneously obtain results for the numerous reaction times. This is discussed in greater detail below.

By way of example and with reference to FIG. 3 showing a microfluidic device 300 for performing a plurality, e.g., 6 time dependent reactions, flow rate is varied along the flow channels 302–312 in order to monitor the time dependent interaction of reactants. In particular, with reference to one flow channel 302, a first reactant is deposited into one reservoir that is coupled to an upstream portion (from the detection zone) of the flow channel 302, e.g., reservoir 322. A second reagent is deposited into a second reservoir, e.g., reservoir 330, that also is coupled to an upstream portion of the flow channel 302.

The reagents are each flowed into flow channel 302 from reservoirs 322 and 330 via channels 322a and 330a, respectively, by either applying a positive pressure to reservoirs 322 and 330 or by applying a negative pressure to one of waste reservoirs 338 or 340. The reagents flow into flow channel 302 and are mixed at intersection 342, whereupon the mixed reagents continue along flow channel 302 past a detection zone 350. The detected reagents then continue through the flow channel 302 into waste channel 340a toward waste reservoir 340. The same operation occurs in parallel in each of flow channels 304–312, transporting reagents from the reservoirs associated with these flow channels. As shown, the flow channels and connecting channels that couple the flow channels to their associated reservoirs are configured so as to provide similar if not identical flow reagents into and through each of flow channels 302–312.

In the case of a single vacuum source applied at waste reservoir 340, variation of the flow rate along the flow channels 302–312 is accomplished by increasing or decreasing the level of vacuum applied at the waste reservoir 340. An optional standard reservoir 338 is also shown. Typically, a dye standard is placed into this well in order to allow auto-focusing of the optical detection system upon channel 338a at detection window 350. The change in vacuum results in a change in the amount of time that the reagents are mixed together prior to detection, e.g., changing the amount of time the reagents are present between intersection 342 and detection zone 350. In the case of the device shown in FIG. 3, up to 6 different reagent mixtures are tested in accordance to the methods described herein. These different reagent mixtures may be combinations of different reagents, or the same reagents at different concentrations.

In some cases, it may be desirable to be able to produce a range of flow rates that is not easily achieved using a single flow channel, vacuum/pressure source combination. Specifically, in a single flow channel, one can generally achieve a particular range of flow rates by varying the motive force applied to the material in that channel due to the responsive range of the controller when combined with a given channel. However, in a system employing multiple flow channels, e.g., flow channels 302–312 in FIG. 3, one can further vary flow rates between channels by varying the flow resistance of the different channels, e.g., by varying their lengths and/or cross-sectional dimensions. Thus, where all the channels of varied resistance are subjected to the same applied motive force, e.g., a vacuum source applied at a single waste reservoir coupled to each channel, the flow rates within the different channels will be different. The flow rate within each of the channels is then further varied by varying the applied motive force, e.g., pressure, vacuum, electric field. One can configure the different channels such that each will operate in a predetermined flow-rate range so as to provide a much wider range of flow rates, and thus reaction times, than is achieved using a single channel. Such configuration methods are described in detail in U.S. patent application Ser. No. 09/238,467, previously incorporated herein by reference.

One can also vary flow resistance within the flow channel by varying the viscosity of the fluid that is being flowed through the channel. Typically, viscosity adjustments to a particular fluid involve the addition of higher viscosity additives to the fluid, or its dilution with a lower viscosity fluid. Typically, viscosity raising additives include, e.g., polymer solutions, e.g., PEG, polyacrylamide, cellulosic polymers, ficoll, polyalcohols, i.e., polyvinylalcohols, glycerol, polypropanol, and the like.

IV. Applications

The methods, devices and systems of the invention are generally used in monitoring reactions, and particularly the kinetic characteristics of those reactions. Generally, reactions include chemical reactions, as well as biochemical and biological reactions between at least two different reagents. Such reactions include simple chemical reactions, e.g., between two or more chemical reagents, to more complex biochemical reactions, e.g., enzyme reactions, binding reactions, signaling reactions, complex cellular reactions, etc.

In preferred aspects, the methods and systems described herein are used in the characterization and/or monitoring of biochemical or biological reactions. Typically such reactions are of particular interest in the biological, biotechnical, diagnostic and/or pharmaceutical fields. Examples of biochemical reactions that are monitored in accordance with the present invention -include simple enzyme reactions, binding reactions between specific binding pairs, e.g., ligandreceptor binding, nucleic acid binding reactions, protein/nucleic acid binding reactions, proteinprotein interactions, and the like, as well as complex cellular reactions, e.g., cellular activation or signaling cascade reactions, cellular viability reactions, or the like.

In the case of simple chemical and/or biochemical reactions, the constituent reagents for the reaction are introduced into and mixed within the flow channel. The reaction mixture is then transported along the flow channel through the detection zone, at which the reaction results are detected. Variation of the flow rate provides a variation in the reaction time after which results are detected, thereby providing a reaction time course. A reaction time course obtained in this manner may use reaction results at a plurality of discrete reaction time points, e.g., based upon a stepping of reaction rates, or may use results from a constantly changing reaction time, e.g., based upon a ramping flow rate. In particular, where specific predetermined reaction times are desired to be monitored, a flow rate is held for a period of time, e.g., from several seconds to several minutes, so as to provide a steady state level of reaction product that is detected. The flow rate of the reagents is then stepped to a different level and held for another time period until a steady state is achieved. The reaction results for each step are correlated with the amount of reaction time for each step. From this data, the reaction kinetics are calculated.

Briefly, the relevant experimental parameters affecting the reaction times (t) in the flow channel system described herein, are the applied pressure differential (P), the hydrodynamic resistance of the channel (R), the reaction channel length (L) between the point of initiation of the reaction and the detection point, and the cross-sectional area of the channel. In the case where all of the reaction constituents move with the bulk fluid velocity, the reaction time for a given pressure gradient P can be expressed as:

$$t = LRA/p$$

Thus, understanding all of the applied parameters of the system, e.g., L, R, A and P, one can determine the reaction time for results obtained at any given pressure. Typically, the system parameters are either measurable or are known from the specifications of the system as produced. The various time-based kinetic parameters of the reaction can then be calculated in accordance with well known procedures (See, e.g., Segel, Biochemical Calculations, 2nd Ed (John Wiley and Sons 1976), incorporated herein by reference in its entirety for all purposes.

In particularly preferred aspects, at least one of the reagents that are being mixed are in the form of whole cell systems. In particular, such systems monitor the interaction of a cell system with another external reagent that is mixed with the cells. This is typically accomplished by monitoring the cell's response to the other reagent. A large number of different cellular responses may be monitored, depending upon the information that is desired. For example, a change in the cell's transport functions, e.g., ion flux, the cell's ability to express gene products, viability or the like are readily monitored as important biological reactions. A variety of such important cell-based reactions are described in co-pending U.S. patent application Ser. No. 09/104,519, filed Jun. 25, 1998, which is incorporated herein by reference in its entirety for all purposes. In accordance with the present invention, the time course of a cellular response to a particular chemical stimulus, e.g., reagent, is monitored over time using the methods described herein. Specifically, a cell suspension is flowed into the flow channel and combined with a particular reagent and the effect of that reagent upon the cells is monitored at the detection zone. The time course of that particular reaction is then monitored by altering the flow rate of the mixture.

The present invention is further illustrated with reference to the following non5 limiting examples.

EXAMPLE 1

Kinetic Analysis

The above-described methods were used to monitor the time dependent response of cell systems to a variety of different chemical stimuli. The device used for analysis was that shown in FIG. 3, and where useful for understanding, the same reference numerals are used.

For the following experiments, two different model systems were used. In the first model system, a non-adherent THP-1 human monocytic leukemia cell line, expressing an endogenous P2 purinergic receptor was exposed to UTP as the ligand, and calcium flux within the cells was monitored. In the second system, an adherent CHO-M1 chinese hamster ovary cell line expressing a transfected M1 muscarinic receptor was exposed to carbachol as the ligand, and again, calcium flux was monitored.

In both systems, the cells were loaded with the calcium-sensitive fluorescent indicator dye Fluo-4 (Molecular Probes). The cells were also stained with a fluorescent nucleic acid stain Syto 62 (Molecular Probes) that ubiquitously stains all cells. The cells were washed and resuspended in isotonic and isopynic buffer (Hank's Balanced Salt Solution (HBSS) pH 7.4, 18% (v/v) Optiprep, 20 mM HEPES, 0.135%BSA, referred to herein as "Buffer A"). The ligand was prepared in six doses (half-log dilutions) in Buffer A.

The channels of a microfluidic device having the channel structure shown in FIG. 3 were flushed with Buffer A. The cell suspension and ligand were added to their respective wells in the microfluidic device, e.g., cell suspensions in wells 314, 318, 322, 324, 326 and 328, and ligand solution in wells 316, 320, 330, 332, 334 and 336. A fluorescein standard was added to the dye well 338 in order to facilitate auto-focusing of the optical detection system. The device was inserted in a modified Agilent 2100 Bioanalyzer that was fitted with a vacuum port that interfaced with waste well 340 of the device. The optical detection system utilized a blue LED as the excitation source and the standard Bioanalyzer optics.

After the run was started, the detector autofocused on the dye channel (338a) and moved sequentially across each of the analysis channels, collecting data from each channel for the entire course of the vacuum variation before moving to the next channel.

Figure 4:
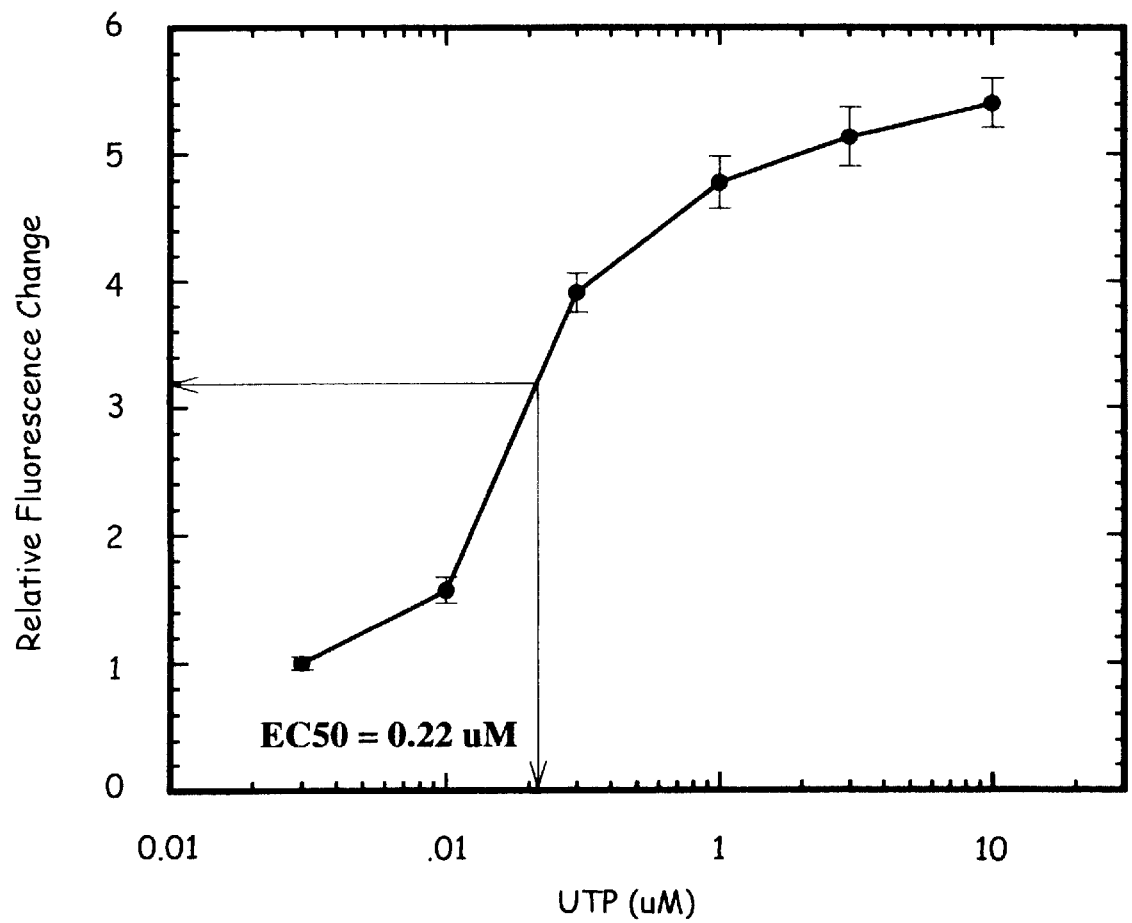
FIG. 4 is a plot of the response kinetics of the P2u receptor to UTP, as measured using the methods and systems of the invention.
Figure 5:
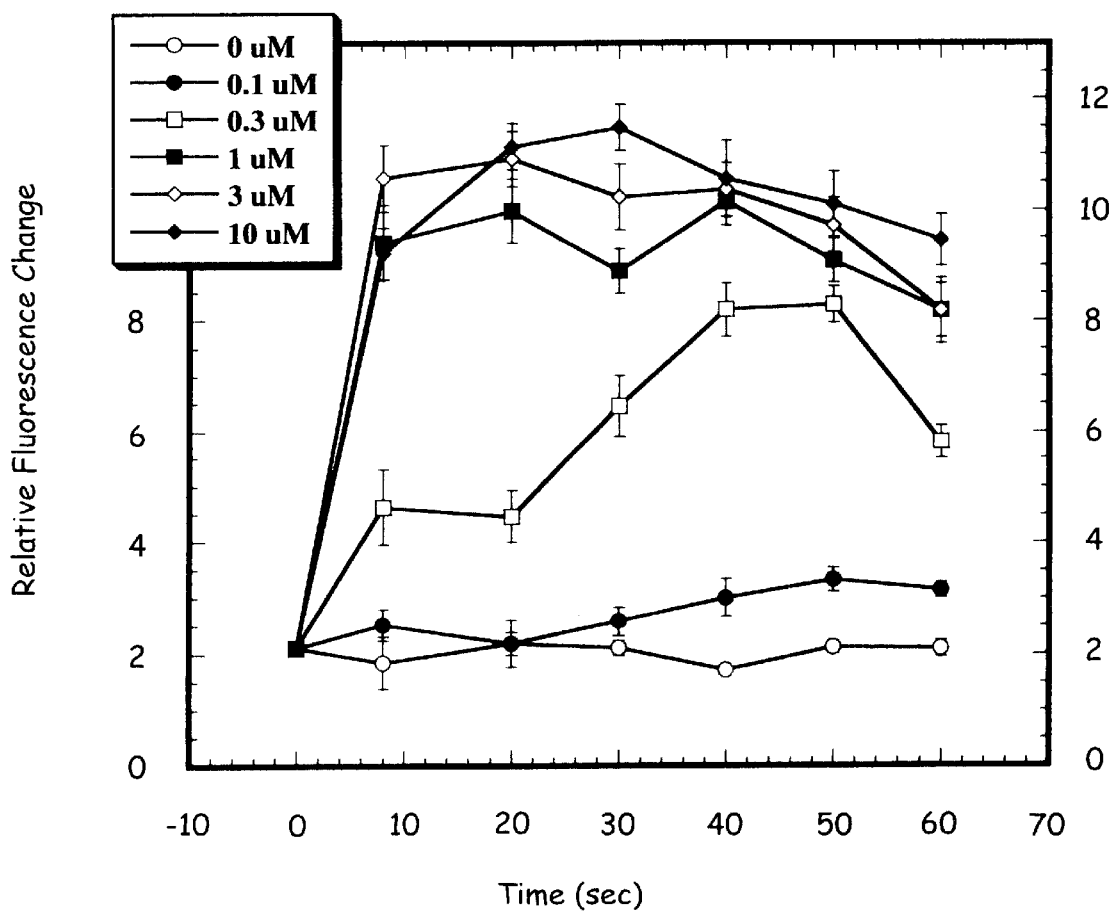
FIG. 5 is a plot of the dose response of the P2u receptor to UTP, from the response kinetics shown in FIG. 4.
Figure 6:
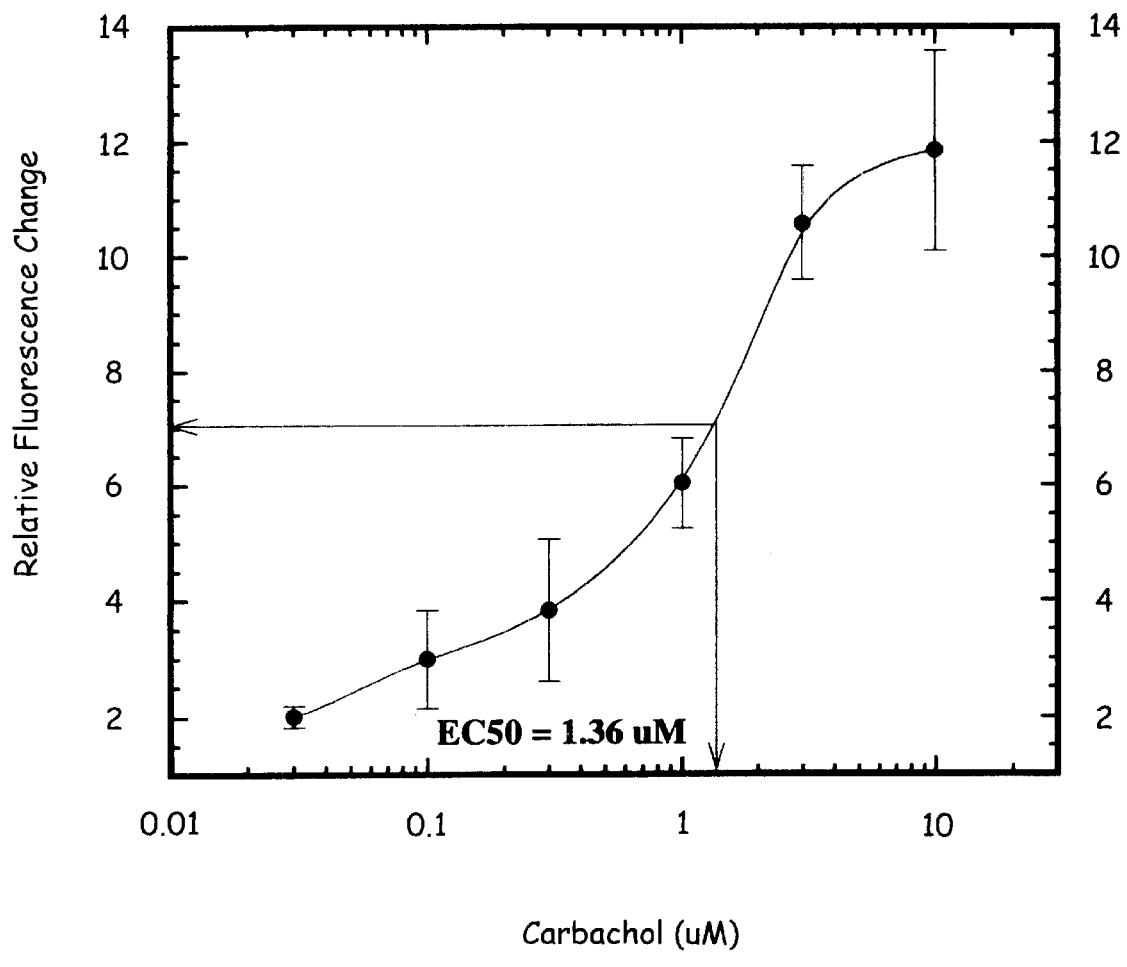
FIG. 6 is a plot of the response kinetics of the M1 muscarinic receptor to Carbachol, as measured using the methods and systems of the invention.
Figure 7:
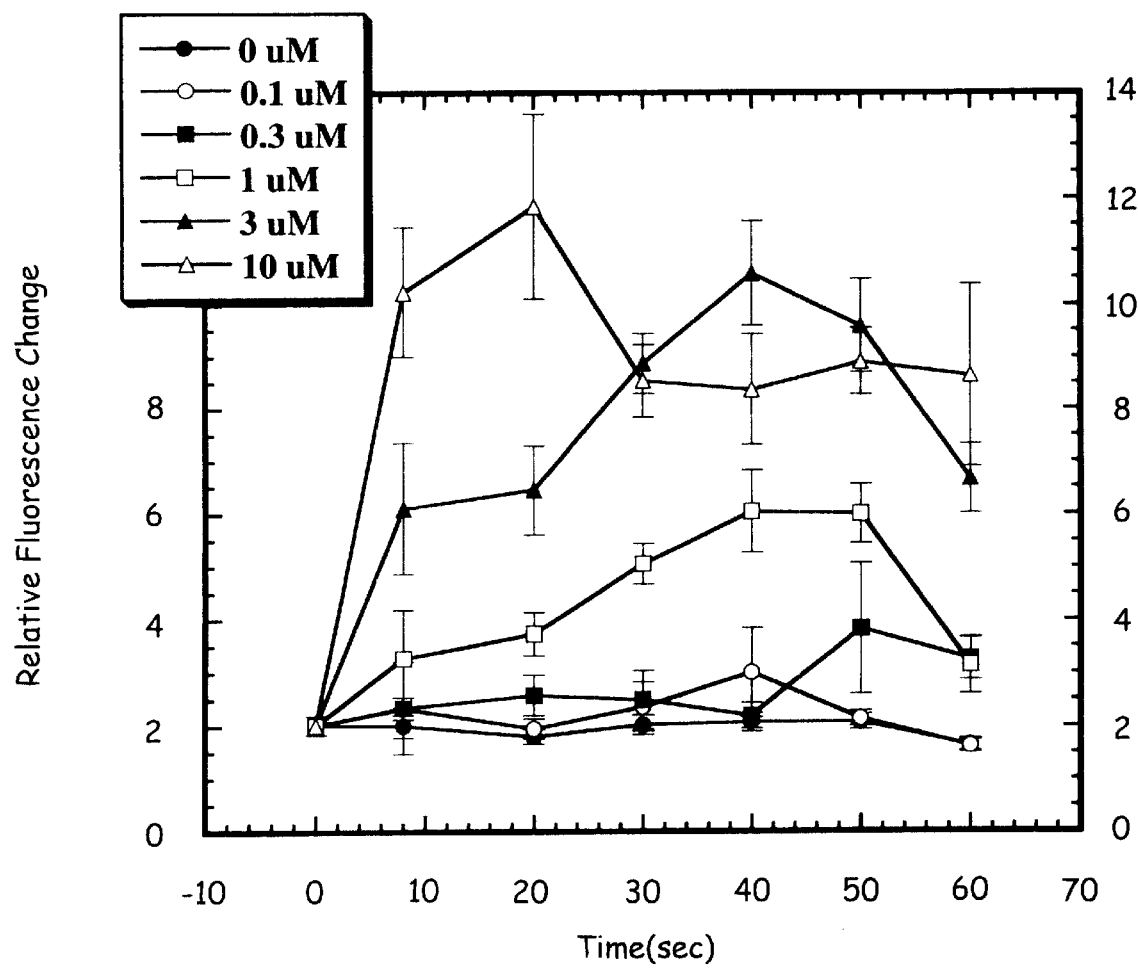
FIG. 7 is a plot of the dose response of the M1 muscarinic receptor to Carbachol, as determined from the response kinetics shown in FIG. 6.

For each channel, the calcium signal was normalized with Syto 62 dye. The mean normalized calcium signal for each pressure step was calculated. The normalized calcium signal was then plotted against the pressure step/incubation time, to generate the kinetic curve of the reaction. FIG. 5 illustrates this curve for the response of the P2u receptor to UTP. FIG. 7 illustrates the same kinetic curve for the response of the M1 muscarinic receptor to Carbachol. The peak response values from the kinetic curves were then plotted against the respective ligand concentration (log) to give the dose response curve for each system, which are shown in FIGS. 4 and 6, for the P2u receptor and M1 muscarinic receptor, respectively.

Unless otherwise specifically noted, ail concentration values provided herein refer to the concentration of a given component as that component was added to a mixture or solution independent of any conversion, dissociation, reaction of that component to alter the component or transform that component into one or more different species once added to the mixture or solution.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of monitoring a time dependent reaction, comprising:
   (i) introducing at least a first reagent into a first flow channel;
   (ii) initiating a reaction involving the at least first reagent, thereby producing a first reaction mixture;
   (iii) transporting the first reaction mixture at a first flow rate along the first flow channel past a detection zone;
   (iv) detecting an extent of the reaction involving the at least first reagent at the detection zone at said first flow rate;
   (v) varying a flow rate of the first reaction mixture along the first flow channel to a second flow rate which is different from said first flow rate; and
   (vi) detecting an extent of the reaction involving the at least first reagent at the detection zone at said second flow rate, thereby providing a reaction time course for the reaction for a plurality of different reaction times.

2. The method of claim 1, wherein the step of initiating the reaction of the first reagent comprises mixing a second reagent with the first reagent to form the reaction mixture.

3. The method of claim 2, wherein at least one of the first and second reagents comprises a cell suspension.

4. The method of claim 2, wherein at least one of the first and second reagents comprises at least one member of a specific binding pair.

5. The method of claim 2, wherein the reaction between the first and second reagents produces an optically detectable signal.

6. The method of claim 5, wherein the optically detectable signal comprises a fluorescent signal.

7. The method of claim 6, wherein the fluorescent signal comprises an increase or decrease in a level of fluorescence in the first flow channel.

8. The method of claim 6, wherein the fluorescent signal comprises a change in an amount of depolarized fluorescence within the first flow channel.

9. The method of claim 2, wherein the first flow channel and at least one of a source of the first reagent and a source of the second reagent are disposed in an integrated body structure.

10. The method of claim 2, wherein the step of varying the flow rate comprises varying an applied pressure differential along the length of the at least first flow channel.

11. The method of claim 10, wherein the step of varying an applied pressure differential along a length of the first flow channel comprises varying a vacuum applied at one end of the first flow channel.

12. The method of claim 10, wherein the step of varying an applied pressure differential along a length of the first flow channel comprises varying a positive pressure applied at one end of the first flow channel.

13. The method of claim 2, further comprising:
   providing at least a second flow channel;
   introducing the first and second reagents into the second flow channel whereupon the first and second reagents mix to form a second reaction mixture, at least one of the first or second reagent being present in the second reaction mixture at a concentration different from its concentration in the first reaction mixture;

varying a flow rate of the second reaction mixture along the second flow channel; and monitoring a result of an interaction between the first and second reagents.

14. The method of claim 13, wherein the steps of varying the flow rate along the first flow channel and varying the flow rate along the second flow channel comprise concurrently applying a varying pressure differential along a length of the first and second flow channels.

15. The method of claim 14, wherein the first and second flow channels are in fluid communication with a common port, and wherein the step of concurrently applying a pressure differential comprises applying a positive pressure or vacuum to the common port.

16. The method of claim 2, further comprising:

providing at least a second flow channel;

introducing third and fourth reagents into the second flow channel whereupon the third and fourth reagents mix to form a second reaction mixture, at least one of the third and fourth reagents being different from the first and second reagents;

varying a flow rate of the second reaction mixture along the second flow channel; and monitoring a result of an interaction between the third and fourth reagents.

17. The method of claim 2, further comprising:

providing at least a second flow channel, the second flow channel having a flow resistance that is different from a flow resistance of the first flow channel;

introducing the first and second reagents into the second flow channel, whereupon the first and second reagents mix to form a second reaction mixture;

varying a flow rate of the second mixture along the second flow channel; and monitoring a result of an interaction between the first and second reagents in the second reaction mixture.

18. The method of claim 17, wherein the steps of varying the flow rate of the first reaction mixture along the first flow channel and the second reaction mixture along the second flow channel comprises applying a single pressure differential across a length of the first and second flow channels, the different flow resistance of the second flow channel from the first flow channel producing a different flow rate of the second reaction mixture through the second flow channel than for the first reaction mixture through the first flow channel.

19. The method of claim 18, wherein the first and second flow channels are fluidly connected to a common port, and the step of varying the flow rate of the first reaction mixture along the first flow channel and the second reaction mixture along the second flow channel comprises applying a positive pressure or vacuum to the common port to move the first and second reaction mixtures through the first and second flow channels, respectively.

20. The method of claim 1, further comprising repeating steps (v) and (vi) at least once at at least a third flow rate which is different from said first and second flow rates to determine the reaction time course for at least three different reaction times.

21. The method of claim 20, further comprising calculating a kinetic curve of the reaction based on the determined reaction time course.

22. The method of claim 1, wherein said first flow rate is faster than said second flow rate.

23. The method of claim 1, wherein said first flow rate is slower than said second flow rate.

* * * * *